United States Patent [19]

Flett

[11] 4,095,949
[45] Jun. 20, 1978

[54] PREPARATION AND MEASUREMENT OF ULTRA MICRO AMOUNTS OF NITROGEN

[76] Inventor: Robert John Flett, 3450 Durocher, Apt. No. 3, Montreal, Quebec, Canada

[21] Appl. No.: 746,225

[22] Filed: Nov. 30, 1976

[30] Foreign Application Priority Data

Dec. 8, 1975 Canada .................................. 241213

[51] Int. Cl.² ............................................ G01N 31/12
[52] U.S. Cl. ............................ 23/230 PC; 23/253 PC
[58] Field of Search .................... 23/230 PC, 253 PC; 73/23.1

[56] References Cited
U.S. PATENT DOCUMENTS

| | | | |
|---|---|---|---|
| 2,382,301 | 8/1945 | Dreher | 23/253 PC |
| 3,241,922 | 3/1966 | Walisch | 23/253 PC |
| 3,252,759 | 5/1966 | Simon | 23/253 PC |
| 3,405,549 | 10/1968 | Finley | 73/23.1 |
| 3,418,514 | 12/1968 | Sternberg | 73/23.1 X |
| 4,004,881 | 1/1977 | Ligon | 23/253 PC X |

Primary Examiner—Robert M. Reese
Attorney, Agent, or Firm—Charles E. Brown

[57] ABSTRACT

This apparatus is useful for converting microgram quantities of particulate nitrogen into nitrogen gas such that it is possible to measure the quantity of nitrogen in the sample as well as to determine the isotopic contents of the nitrogen by spectrometric means. This apparatus constitutes an improvement over prior art inventions in that it is easier to operate and/or less expensive to build than was the case for similar previously known inventions.

12 Claims, 3 Drawing Figures

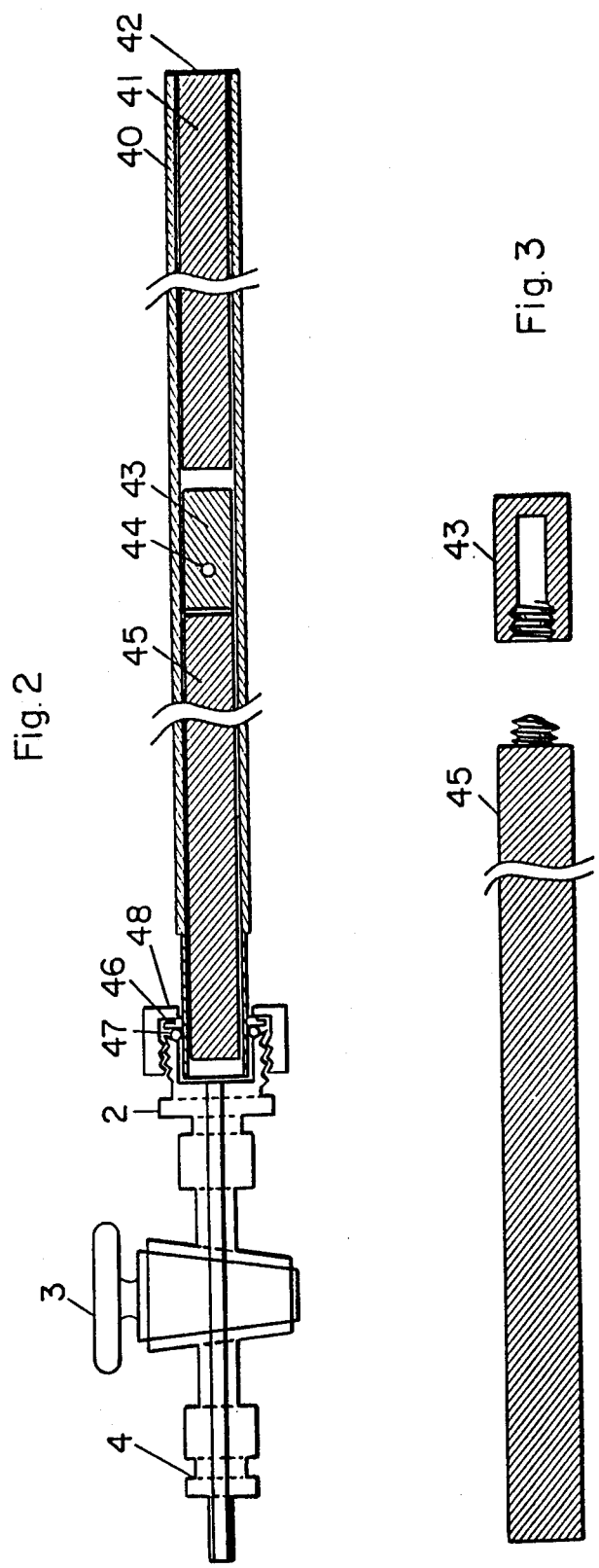

PREPARATION AND MEASUREMENT OF ULTRA MICRO AMOUNTS OF NITROGEN

BACKGROUND OF THE INVENTION (a) Field of the Invention

This invention relates to an improved apparatus and method for the determination of the nitrogen content of nitrogen-containing matter; more especially the invention is concerned with a method and apparatus for the preparation and measurement of ultra micro amounts of nitrogen gas produced by the combustion of particulate matter in an oxygen environment.

(b) Description of Prior Art

Conventional determinations of nitrogen isotope ratios have been performed in several ways. The most common method has been to do Kjeldahl digestions of the substance being analysed. When properly executed the nitrogen is converted to ammonium sulfate and it is then distilled into a weak acid, an aliquot of which is subsequently back titrated so that the quantity of nitrogen can be calculated. The remaining dissolved ammonium salt is concentrated by evaporation and is then reacted in vacuo with alkaline hypobromite, the product being nitrogen gas. The nitrogen next passes through a liquid nitrogen trap before entering a mass spectrometer for isotope ratio analysis. The same sample preparation procedure has been extensively used for emission spectrometric analysis of isotope ratios.

The Dumas procedure has also been widely used for sample preparation. It is particularly useful because the sample is converted directly from particulate material to nitrogen gas. Unfortunately the manual methods are rather slow and tedious. An automated Dumas method has been developed, however, and it has been successfully connected to a mass spectrometer to enable rapid mass ratio analysis. The disadvantages are that initial costs are high, several qualified personnel are needed to operate the apparati, and the quantity of nitrogen produced is not concurrently measured.

The Dumas procedure has also been applied to emission spectrometers and has been shown to be successful with extremely small amounts of ammonium chloride. However, sample preparation is long and tedious.

SUMMARY OF THE INVENTION

A primary object of the present invention is to provide an improved method and apparatus for the determination of the nitrogen content of nitrogen-containing matter.

A further object of the present invention is to provide a simple, inexpensive and fairly rapid preparation unit for stable nitrogen isotope spectrometry, especially emission spectrometry. An emission spectrometer, which is much less expensive to purchase and operate than a mass spectrometer, connected to an inexpensive preparation unit can make nitrogen isotope analysis much more practical for many people.

Another object of this invention is to provide a relatively simple method and apparatus for measuring of the amount of nitrogen in a sample being prepared for isotope analysis. Such a measure would be especially valuable in studies concerning biological uptake of labelled nitrogen or labelled nitrogen containing compounds.

Another object of this invention is to provide a method and apparatus enabling the successful analysis of samples containing as little as 10 micrograms of nitrogen. Some prior art methods are capable of handling such small quantities of nitrogen but they are either much more troublesome or expensive.

According to one aspect of the invention there is provided an ultra micro analysis apparatus, which has small internal volume, for the determination of the nitrogen content of nitrogen containing matter. The apparatus comprises a system which includes a combustion tube which communicates via a conduit means with a measuring means for measuring the amount of nitrogen gas in the system. First means is provided in the conduit means for removing non-nitrogen-containing gases from the gaseous state and for converting gaseous nitrogen oxides to nitrogen gas, so that all the nitrogen in the sample undergoing investigation is in the system in the gaseous state. The system is adapted for communication with an evacuation means for the controlled evacuation of the apparatus. A first vacuum tight valve means is disposed in the conduit means between the combustion tube and the aforementioned first means. Means is further provided which is adapted to communicate the combustion tube with an oxygen gas introducing means for introducing oxygen to the combustion tube.

According to another aspect of the invention there is provided an ultra micro analysis apparatus, which has small internal volume, for the determination of the nitrogen content of nitrogen-containing matter. The apparatus comprises a system which includes a combustion tube which communicates via a conduit means with a spectrometer for the spectrometric analysis of nitrogen in the system. First means is provided in the conduit means for removing non-nitrogen-containing gases from the gaseous state and for converting gaseous nitrogen oxides to nitrogen gas, so that all the nitrogen in the sample undergoing investigation is in the system in the gaseous state. The system is adapted for communication with an evacuation means for the controlled evacuation of the apparatus. A first vacuum tight valve means is disposed in the conduit means between the combustion tube and the aforementioned first means. Means is further provided which is adapted to communicate the combustion tube with an oxygen gas introducing means for introducing oxygen to the combustion tube.

In an especially preferred form of the invention the ultra micro analysis apparatus includes both the means for measuring the amount of nitrogen in the system and the spectrometer for determining the ratio of the different nitrogen isotopes.

According to a different aspect of the invention there are provided methods for determining the nitrogen content of nitrogen containing matter employing the ultra micro analysis apparatus of the invention.

According to yet another aspect of the invention there is provided a combustion apparatus for use in ultra micro analysis comprising a hollow elongated refractory tube, sealing means for maintaining a vacuum in said tube, sample holding means adapted to be contained in said tube and at least one refractory filler rod occupying most of the vacant tube volume effective to minimize the internal volume of the tube.

BREIF DESCRIPTION OF DRAWINGS

These and other objects and advantages of the invention will be apparent from the following description, when read in conjunction with the accompanying drawings, in which:

FIG. 1 is a semi-diagrammatic illustration of a complete preparation unit including a feedline to an electrodeless discharge tube that fits into an emission spectrometer, FIG. 2 is a sectional view through a combustion tube, with filler rod and sample cup in place, showing an installed vacuum tight closure with attached valve and quick connect fitting, and FIG. 3 is a sectional view of the filler rod and sample cup, in this case, the sample cup screwing onto the filler rod.

DESCRIPTION OF PREFERRED EMBODIMENTS

Figure 1:
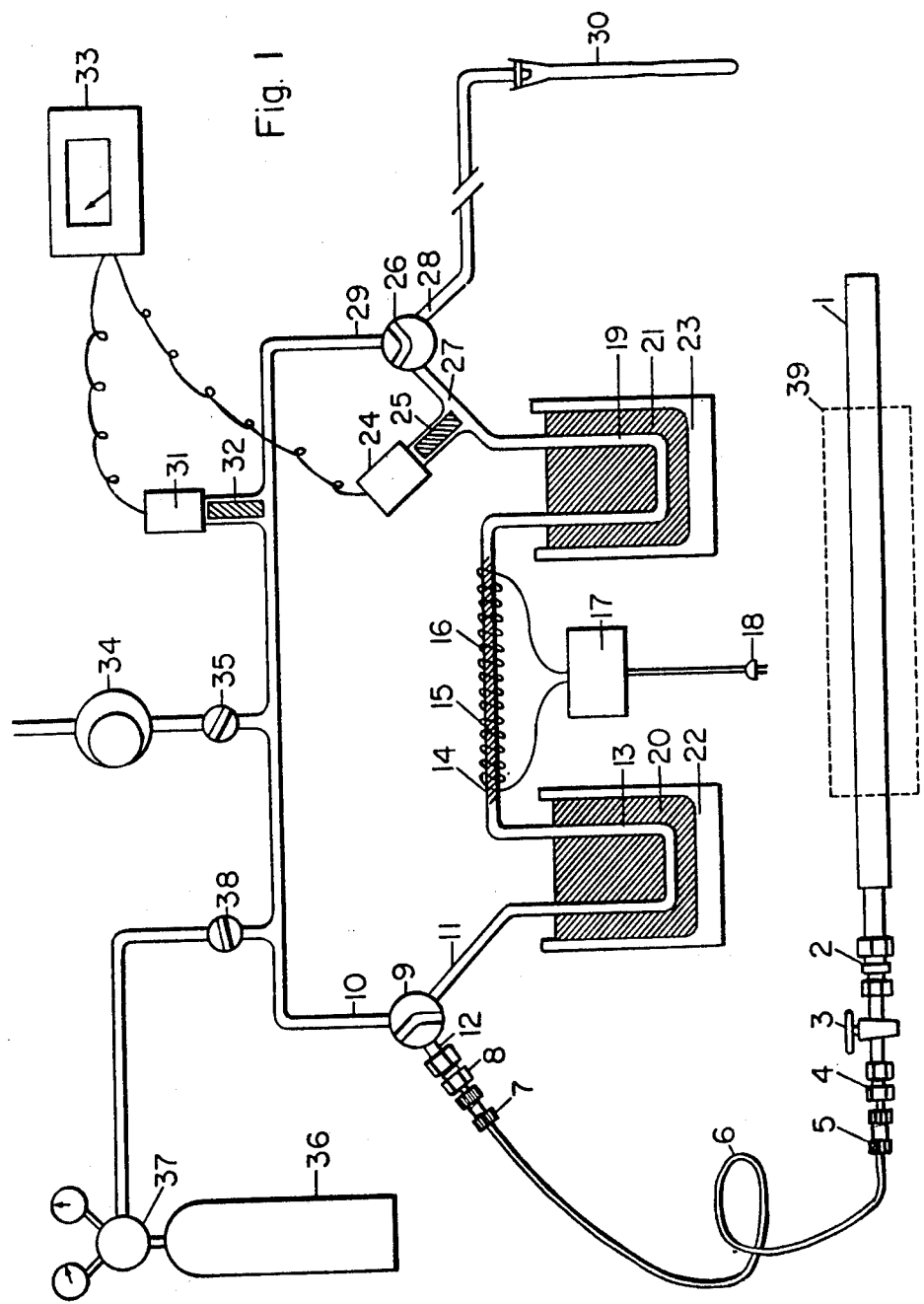

With further reference to FIG. 1, a combustion tube 1 wherein the sample is placed has vacuum tight 'O' ring closure 2, valve assembly 3 and quick connect fitting 4 respectively. A flexible conduit 6 is used to link quick connect fittings 8 and 4 through vacuum tight unions 7 and 5. A valve 9 serves to completely isolate the combustion tube 1 from the rest of the apparatus, to selectively connect the combustion tube to either the legs 10 or 11, or to connect legs 10 and 11 together. These connections and more are also possible by the use of three simple valves instead of the three way valve 9 shown. This is accomplished by placing a valve in each of legs 10, 11 and 12 immediately before they form a union.

A cold trap 13 is shown immersed in liquid nitrogen 20 which is contained by Dewar 22. A glass reduction tube 14 contains reduced copper turnings 15 and is heated by resistance wire 16 wound around the tube, the power being supplied via a variable transformer 17 which is in turn coupled to an A.C. supply by plug 18. A second cold trap 19 is cooled by liquid nitrogen 21 contained in Dewar 23. A vacuum guage sending unit 24 has its internal volume reduced by a filler rod 25. A valve 26 serves to selectively evacuate the reduction tube 14 and cold traps 13 and 19 via leg 27, to selectively evacuate an electrodeless discharge tube 30 via leg 28, to conduct gases from the cold traps 13 and 19 and reduction tube 14 to the electrodeless discharge tube 30, and to seal leg 27. These connections and more are also possible by the use of three simple valves instead of the three way valve 26 shown. This is accomplished by placing a valve in each of legs 27, 28 and 29 immediately before they form a union.

The vacuum guage sending unit 31 has its internal volume reduced by filler rod 32. The pressure readings from both sending units 24 and 31 are shown, in this particular configuration, being sent to a dual channel receiver and display unit 33. The vacuum pump 34 is employed to evacuate the apparatus and it is isolated from the apparatus by vacuum exhaust valve 35. Ultra high purity oxygen 36 is supplied at approximately 2 lb/in² to the apparatus through a two stage regulator 37 and a valve 38.

A sectional view of the combustion tube 1, (as identified in FIG. 1), heated by tube furnace 39, is shown in FIG. 2. The stainless steel combustion tube wall is designated by the numeral 40. In this configuration, the filler rod 41 is welded at 42 into the combustion tube and thereby seals the tube end. The sample cup 43 is in this case shown to have a vent hole 44 and be attached to the filler rod 45.

FIG. 3 is a sectional view of the filler rod 45 and sample cup 43. In this particular configuration, the filler rod 45 is shown to screw into the sample cup 43 and thereby serves as a cap for the cup.

Referring again to FIG. 2, a sectional view of union 2 is shown. The union 2 screws into the nut 48 which in turn compresses the flange 46 onto the 'O' ring 47 which makes the seal between the combustion tube 1 and the union 2.

A normal operating cycle would begin by completely evacuating the entire preparation unit with valve 38 being closed. During evacuation valve 9 is connecting legs 10 and 11 and valve 26 is connecting legs 29 and 28. The reduction tube 14 is brought to a dull red heat that is visible only in the dark and it is never cooled. The combustion tube furnace is heated during working hours to 800° C. A dry sample containing 10 - 200 micrograms particulate nitrogen-containing matter is placed on a small piece of aluminum foil which is subsequently folded into a small size and fitted into the sample cup 43. The aluminum foil prevents the buildup of ash, or in cases where glass fibre filters are combusted, prevents glass from melting and sticking to the sample cup. The sample cup is then screwed onto the filler rod 45 and the two pieces inserted into the combustion tube 1 as seen in FIG. 2. The vacuum tight 'O' ring closure 2, valve assembly 3 and quick connect fitting 4 are fitted as a unit to the combustion tube 1 and then vacuum sealed by tightening nut 48. The quick connect fitting 4 is inserted into the vacuum tight union 5 which is then sealed finger tight. The valve 9 is turned to connect legs 12 and 10, valve 3 is opened and the sample is evacuated to a constant pressure <4 milli Torri as measured by sending unit 31 and vacuum guage 33. The Dewars 22 and 23 are filled with liquid nitrogen and are maintained at least 90% full during sample preparation and measurement. The pressure, as determined by the sending unit 24 and vacuum guage 33, should read 0 milli Torri when the cold traps 13 and 19 and the reduction furnace 14 are fully pumped down. Complete evacuation is not possible without cooling the cold traps because condensable gases are given off by the hot copper turnings. After several minutes of pumping, the period being inversely proportional to the dryness of the sample, the required pressure of <4 milli Torri as measured by vacuum sender 31, will be met and the vacuum exhaust valve 35 is closed. Valve 38 is opened and oxygen is allowed into the combustion tube 1 at approximately 2 lb/in² final pressure. The valve 38 is closed, the valve 35 opened and the oxygen pumped away, thereby effecting a rinse of the combustion tube 1. After the pressure at vacuum sender 31 has again dropped below 4 milli Torri the valve 35 is closed and oxygen is again added at approximately 2 lb/in² to the combustion tube 1 via valve 38. The valves 3 and 38 are then closed and vacuum exhaust valve 35 is opened so as to evacuate the excess oxygen from the apparatus. The combustion tube 1 is now placed into the nearby tube furnace 39, the movement of the combustion tube being possible due to the flexability of the conduit 6. Both ends of the combustion tube 1 protrude far enough from the furnace such that they are not heated considerably. This allows the 'O' ring to maintain an effective seal on the one end and prevents the weld at the other end from being stressed by repeated heating and cooling cycles. The combustion of the sample is allowed to proceed at 800° C for a minimum of 5 minutes. During the combustion period, the pressure indicated by the vacuum sender 24 is checked and if the pressure is above 0 milli Torri, the cold trap and reduction tube are again evacuated by setting valve 9 such that legs 10 and 11 connect and by setting valve 26 such that legs 29 and 27 connect. After this evacuation, valve 9 is set to connect legs 12 and 11 and valve 26 is set to connect legs 29 and 28. If the pressure, as indicated by vacuum sender 31, is above 4 milli Torri, evacuation is allowed to proceed until the pressure is suitably reduced. At the end of the 5 minute combustion period, valve 3 is opened and the gases contained in the combustion tube pass into the first cold trap 13. In this cold trap, water vapour, carbon dioxide as well as some other condensables are frozen out and some of the unused oxygen is liquified. The nitrogen gas, nitrogen oxides, and the remainder of the unused oxygen then pass through the hot copper turnings 15 of the reduction tube 14. The excess oxygen reacts with the copper to form copper oxide and the oxides of nitrogen are reduced to nitrogen gas as they pass through the hot copper. Any gross impurities remaining in the nitrogen gas are next removed by the cold trap 19. The pressure reading, as indicated by vacuum sender 24, reaches a maximum value after a period of approximately 30 seconds. This pressure reading is directly proportional to the amount of nitrogen in the sample and therefore the quantity of nitrogen in the sample can easily be determined using a suitable standard curve or mathematical relation. After the pressure of nitrogen gas has been determined, valve 26 is set such that legs 27 and 28 join. The nitrogen gas then passes into the electrodeless discharge tube 30 where it is ready for emission spectrometric analysis, provided the pressure is within suitable limits. If the vacuum sender 24 indicates the pressure to be excessive for accurate analysis, then valve 26 can be used to partially evacuate the nitrogen gas before it is transferred to the discharge tube 30.

It should be appreciated that the direct connection between the combustion tube 1 and the electrodeless discharge tube 30 is advantageous because it allows emissions to proceed for relatively longer periods of time due to the large reservoir of nitrogen gas available to feed the discharge tube. Also, in the configuration shown in FIG. 1, the discharge tube 30 can be evacuated while still being excited, this process now being known to remove memory of previous samples from the discharge tube.

The minimum cycling time of the apparatus is 20 minutes; 5 minutes are required for optical scanning of the emissions and a further 15 minutes are required to clean up the discharge tube by excitation under vacuum. The evacuation of the apparatus and next sample, as well as the combustion cycle are done simultaneously with discharge tube clean up.

It should also be appreciated that the copper turnings 15 in the reduction tube 14 need not be replaced after many combustion cycles when they become oxidized but may be easily reduced in situ by the passage of hydrogen gas over them while being heated. The use of a glass reduction tube allows the extent of the copper oxidation to be checked visually.

A further convenience is the fact that the cold traps need only be brought to room temperature once a day in order to remove the accumulated water, carbon dioxide and other condensables. Such heating is best performed at the end of the working day and is easily accomplished by removing the Dewars from the cold traps for a period extending to the next day that the apparatus is used.

The apparatus and method are especially suitable for the determination of the content of different nitrogen isotopes in particulate organic matter. The apparatus and method are not especially appropriate for determining the nitrogen in liquids which vapourize under the vacuum evacuation conditions.

It will be recognized that the apparatus can be readily calibrated employing samples in which the nitrogen content is known; in particular the vacuum guage may be calibrated so that the amount of nitrogen in the system can be read directly.

Other advantages and modifications will also occur to those skilled in the art. It is not my intention to limit my invention other than is necessitated by the scope of the appended claims.

I claim:

1. An ultra micro analysis apparatus of small internal volume for determination of the nitrogen content of nitrogen-containing matter comprising a system which comprises a combustion tube communicating via conduit means with measuring means for measuring the amount of nitrogen in the system; and first means disposed in said conduit means for removing non-nitrogen-containing gaseous combustion products of said matter from the gaseous state and for converting gaseous nitrogen oxides to nitrogen gas; said system being adapted for communication with evacuation means for controlled evacuation of the apparatus; a first vacuum tight valve means disposed in said conduit means between said combustion tube and said first means; and including means to communicate said combustion tube with means for introducing oxygen gas to the combustion tube.

2. An apparatus according to claim 1, wherein said first means disposed in said conduit means comprises first and second cold traps for condensing or solidifying said gaseous combustion products, and a reduction tube interconnecting said traps for reducing oxides of nitrogen to nitrogen and removing unconsumed oxygen; and said measuring means comprises a vacuum gauge for measuring nitrogen pressure; and further including furnace means for said reduction tube and furnace means for said combustion tube.

3. An ultra micro analysis apparatus of small internal volume for determination of the nitrogen content of nitrogen-containing matter comprising a system which comprises a combustion tube communicating via conduit means with a spectrometer for the stable isotope spectrometric analysis of nitrogen, and first means disposed in said conduit means for removing non-nitrogen-containing gaseous combustion products of said matter from the gaseous state and for converting gaseous nitrogen oxides to nitrogen gas; said system being adapted for communication with evacuation means for controlled evacuation of the apparatus; a first vacuum tight valve means disposed in said conduit means between said combustion tube and said first means; and including means to communicate said combustion tube with means for introducing oxygen gas to the combustion tube.

4. An apparatus according to claim 3, wherein said first means disposed in said conduit means comprises first and second cold traps for condensing or solidifying said gaseous combustion products, and a reduction tube interconnecting said traps for reducing oxides of nitrogen to nitrogen and removing unconsumed oxygen; and further including furnace means for said reduction tube and furnace means for said combustion tube.

5. An ultra micro analysis apparatus of small internal volume for determination of the nitrogen content of nitrogen-containing matter comprising a system which comprises a combustion tube communicating via conduit means with a spectrometer for the stable isotope spectrometric analysis of nitrogen, measuring means disposed in said conduit means to measure the amount of nitrogen in the system; and first means disposed in said conduit means for removing non-nitrogen-containing gaseous combustion products of said matter from the gaseous state and for converting gaseous nitrogen oxides to nitrogen gas; said system being adapted for communication with evacuation means for controlled evacuation of the apparatus; a first vacuum tight valve means disposed in said conduit means between said combustion tube and said first means; and including means to communicate said combustion tube with means for introducing oxygen gas to the combustion tube.

6. An apparatus according to claim 5, wherein said first means disposed in said conduit means comprises first and second cold traps for condensing or solidifying gases other than nitrogen, and a reduction tube interconnecting said traps for reducing oxides of nitrogen to nitrogen and removing unconsumed oxygen; and said measuring means comprises a vacuum guage for measuring nitrogen pressure; and further including furnance means for said reduction tube and furnace means for said combustion tube.

7. An apparatus according to claim 5, including a second vacuum tight valve means disposed in said conduit means between said measuring means and said spectrometer for directing the nitrogen gas to the spectrometer.

8. A method for the micro analysis of nitrogen-containing matter to determine the nitrogen content which comprises:
  i. providing an evacuated system including a combustion tube containing a micro sample of nitrogen-containing matter.
  ii. introducing oxygen gas to said combustion tube and combusting said micro sample,
  iii. converting gaseous nitrogen oxides formed in said combusting to nitrogen and removing non-nitrogen containing gases produced in said combustion from the gaseous state such that said system contains the nitrogen of said micro-sample in a gaseous state,
  iv. measuring the amount of gaseous nitrogen and spectrometrically determining the nitrogen stable isotope ratio.

9. A method according to claim 8, in which (in step iii) gases other than nitrogen and nitrogen oxides from said combusting are condensed or solidified in a first cold trap means, whereafter oxides of nitrogen are reduced to nitrogen, oxygen is removed by formation of copper oxides and residual gases other than nitrogen are condensed or solidified in a second cold trap means; and (in step iv) said measuring comprises determining the nitrogen pressure with a vacuum gauage.

10. An ultra micro analysis apparatus of small internal volume for determination of the nitrogen content of nitrogen-containing matter comprising a system which comprises a combustion tube communicating via a first conduit means with a spectrometer for the stable isotope spectrometric analysis of nitrogen, measuring means disposed in said first conduit means to measure the amount of nitrogen in the system; and first means disposed in said conduit means for removing non-nitrogen-containing gaseous combustion products of said matter from the gaseous state and for converting gaseous nitrogen oxides to nitrogen gas; said system communicating via a second conduit means with evacuation means for controlled evacuation of the apparatus; a first vacuum tight valve means disposed in said first conduit means between said combustion tube and said first means; and including third conduit means communicating said combustion tube with means for introducing oxygen gas to the combustion tube.

11. An apparatus according to claim 10, wherein said spectrometer is an emission spectrometer; and said measuring means comprises a vacuum gauge for measuring nitrogen pressure.

12. An apparatus according to claim 11, wherein said first means comprises first and second cold traps for condensing or solidifying said gaseous combustion products, and a reduction tube interconnecting said traps for reducing oxides of nitrogen to nitrogen and removing unconsumed oxygen.

* * * * *